(12) United States Patent
Chen et al.

(10) Patent No.: US 6,702,736 B2
(45) Date of Patent: *Mar. 9, 2004

(54) ANATOMICAL VISUALIZATION SYSTEM

(76) Inventors: David T. Chen, 12 Sunset Rd., Somerville, MA (US) 02144; Steven D. Pieper, Gove Hill Rd., Thetford Center, VT (US) 05075; Michael A. McKenna, 232 Broadway, Cambridge, MA (US) 02139

( * ) Notice: Subject to any disclaimer, the term of this patent is extended or adjusted under 35 U.S.C. 154(b) by 0 days.

This patent is subject to a terminal disclaimer.

(21) Appl. No.: 10/104,082

(22) Filed: Mar. 21, 2002

(65) Prior Publication Data

US 2003/0018235 A1 Jan. 23, 2003

Related U.S. Application Data

(63) Continuation-in-part of application No. 09/874,869, filed on Jun. 5, 2001, which is a continuation of application No. 09/111,431, filed on Jul. 7, 1998, now Pat. No. 6,241,657, which is a continuation of application No. 08/505,587, filed on Jul. 24, 1995, now Pat. No. 5,776,050.

(60) Provisional application No. 60/277,643, filed on Mar. 21, 2001.

(51) Int. Cl.$^7$ .............................. A61B 1/00; A61B 5/05
(52) U.S. Cl. ..................... 600/117; 600/407; 600/479
(58) Field of Search ........................ 600/101, 103, 600/109, 117, 118, 407, 476; 348/65, 74; 606/130

(56) References Cited

U.S. PATENT DOCUMENTS 4,722,056 A * 1/1988 Roberts et al. ............. 606/130
4,729,098 A    3/1988 Cline et al.
4,882,679 A   11/1989 Tuy et al.
4,922,909 A *  5/1990 Little et al. ................. 600/300

(List continued on next page.)

OTHER PUBLICATIONS

Kawata et al., "Three Dimensional Imaging of Blood Vessels Using Cone–Beam CT", IEEE Comput. Soc. Press, Proceedings ICIP 94, vol. 2, pp. 140–144.

Klein et al., "Identifying Vascular Features With Orientation Specific Filters and B–Spline Snakes", IEEE Comput. Soc. Press, Computers in Cardiology 1994, pp. 113–116.

(List continued on next page.)

*Primary Examiner*—John P. Leubecker
(74) *Attorney, Agent, or Firm*—Pandiscio & Pandiscio, P.C.

(57) ABSTRACT

A real-time computer-based viewing system is disclosed comprising a database of pre-existing software objects, wherein at least one of the software objects corresponds to a physical structure which is to be viewed by the system and at least one of the software objects corresponds to a graft which is to be deployed adjacent the physical structure, a real-time sensor for acquiring data about the physical structure when the physical structure is located within that sensor's data acquisition field, generating means for generating an additional software object corresponding to the physical structure using data acquired by the sensor, registration means for positioning the additional software object in registration with the pre-existing software objects contained in the database, and processing means for generating an image from the software objects contained in the database, based upon a specified point of view.

1 Claim, 14 Drawing Sheets

U.S. PATENT DOCUMENTS

| | | | |
|---|---|---|---|
| 4,945,478 A | | 7/1990 | Merickel et al. |
| 4,965,844 A | | 10/1990 | Oka et al. |
| 4,985,855 A | | 1/1991 | Aldrich et al. |
| 4,989,083 A | * | 1/1991 | Eino .......................... 348/135 |
| 5,005,559 A | | 4/1991 | Blanco et al. |
| 5,151,856 A | | 9/1992 | Halmann et al. |
| 5,153,721 A | * | 10/1992 | Eino et al. .................. 382/152 |
| 5,179,638 A | | 1/1993 | Dawson et al. |
| 5,230,623 A | | 7/1993 | Guthrie et al. |
| 5,231,483 A | | 7/1993 | Sieber et al. |
| 5,255,352 A | | 10/1993 | Falk |
| 5,261,404 A | * | 11/1993 | Mick et al. ................. 600/425 |
| 5,274,551 A | | 12/1993 | Corby, Jr. |
| 5,291,889 A | | 3/1994 | Kenet et al. |
| 5,295,199 A | | 3/1994 | Shino |
| 5,297,215 A | | 3/1994 | Yamagishi |
| 5,319,551 A | | 6/1994 | Sekiguchi et al. |
| 5,329,310 A | | 7/1994 | Liljegren et al. |
| 5,363,476 A | | 11/1994 | Kurashige et al. |
| 5,378,915 A | | 1/1995 | Hines et al. |
| 5,383,454 A | | 1/1995 | Bucholz |
| 5,384,594 A | | 1/1995 | Sieber et al. |
| 5,398,684 A | | 3/1995 | Hardy |
| 5,417,210 A | * | 5/1995 | Funda et al. ................ 600/425 |
| 5,447,154 A | | 9/1995 | Cinquin et al. |
| 5,448,687 A | | 9/1995 | Hoogerhyde et al. |
| 5,461,706 A | | 10/1995 | Trow et al. |
| 5,491,510 A | * | 2/1996 | Gove .......................... 348/77 |
| 5,493,595 A | | 2/1996 | Schoolman |
| 5,497,452 A | | 3/1996 | Shimizu et al. |
| 5,511,153 A | | 4/1996 | Azarbayejani et al. |
| 5,526,812 A | * | 6/1996 | Dumoulin et al. .......... 600/407 |
| 5,526,814 A | * | 6/1996 | Cline et al. ................. 600/411 |
| 5,531,227 A | | 7/1996 | Schneider |
| 5,537,638 A | | 7/1996 | Morita et al. |
| 5,558,619 A | * | 9/1996 | Kami et al. ................. 600/146 |
| 5,704,897 A | * | 1/1998 | Truppe ........................ 600/117 |
| 5,765,561 A | * | 6/1998 | Chen et al. ................. 600/407 |
| 5,873,822 A | * | 2/1999 | Ferre et al. ................. 600/407 |

OTHER PUBLICATIONS

Chen et al., "Left Ventricle Global Motion and Shape From CT Volumetric Data", IEEE Apr. 1993, V–101 to V–104 (reprint).

Vandroden, "Don't Look Now, But a Body Has Been Found in the Basement of Cummings Hall", Dartmouth Thayer School of Engineering Directions, a periodical published by the Trustees of Dartmouth College, Hanover, New Hampshire, vol. 8, No. 1, Fall 1993, pp. 30–36.

Roberts et al., "A frameless stereotaxic integration of computerized tomographic imaging and the operating microscope", J. Neurosurg./vol. 65/ Oct. 1986, pp. 545–549.

Weisburn et al., "An Interactive graphics editor for 3D Surgical simulation", SPIE vol. 626 Medicine XIV/PACS IV (1986), pp. 483–490.

Shalev et al., "Pseudo–3D imaging with the DICON–8", SPIE vol. 555 Medical Imaging and Instrumentation '85 (1985), pp. 63–66.

Fowler, "Computers May Drive Revolution in Neurosurgery Techniques", Washington Post, Science, Aug. 15, 1994.

Applicants' "IRA Magazine Demo (SeeTM)" displayed Jun. 1993 (24 minutes).

* cited by examiner

UNIT DISK

| VERTEX | XYZ | UV |
|--------|-----|-----|
| $V_1$ | 0 -.5 | .5 .987 |
| $V_2$ | .044 -.498 0 | .53 .986 |
| $V_3$ | .087 -.492 0 | .56 .980 |
| ... | ... | ... |

THIS IS A SCHEMATIC REPRESENTATION OF A UNIT DISK SOFTWARE OBJECT WHERE SAID DISK IS DEFINED IN THE X-Y PLANE AND HAS A DIAMETER OF 1.

ANATOMICAL VISUALIZATION SYSTEM

This application:

(1) is a continuation-in-part of pending prior U.S. patent application Ser. No. 09/874,869, filed Jun. 5, 2001 by David T. Chen et al. for ANATOMICAL VISUALIZATION SYSTEM, which in turn is a continuation of U.S. patent application Ser. No. 09/111,431, filed Jul. 7, 1998, by David T. Chen et al. for ANATOMICAL VISUALIZATION SYSTEM, now U.S. Pat. No. 6,241,657, which in turn is a continuation of prior U.S. patent application Ser. No. 08/505,587, filed Jul. 24, 1995 by David T. Chen et al. for ANATOMICAL VISUALIZATION SYSTEM, now U.S. Pat. No. 5,776,050, which patent applications are hereby incorporated herein by reference; and (2) claims benefit of pending prior U.S. Provisional Patent Application Ser. No. 60/277,643, filed Mar. 21, 2001 by David T. Chen et al. for ANATOMICAL VISUALIZATION SYSTEM, which patent application is hereby incorporated herein by reference.

FIELD OF THE INVENTION

This invention relates to medical apparatus in general, and more particularly to anatomical visualization systems.

BACKGROUND OF THE INVENTION

Endoscopic surgical procedures are now becoming increasingly popular due to the greatly reduced patient recovery times resulting from such surgery.

More particularly, in endoscopic surgical procedures, relatively narrow surgical instruments are inserted into the interior of the patient's body so that the distal (i.e., working) ends of the instruments are positioned at a remote interior surgical site, while the proximal (i.e., handle) ends of the instruments remain outside the patient's body. The physician then manipulates the proximal (i.e., handle) ends of the instruments as required so as to cause the distal (i.e., working) ends of the instruments to carry out the desired surgical procedure at the remote interior surgical site. As a result of this technique, the incisions made in the patient's body can remain relatively small, thereby resulting in significantly faster patient recovery times.

By way of example, laparoscopic surgical procedures have been developed wherein the abdominal region of the patient is inflated with gas (e.g., $CO_2$) and then surgical instruments are inserted into the interior of the abdominal cavity so as to carry out the desired surgical procedure. By way of further example, arthroscopic surgical procedures have been developed wherein a knee joint is inflated with a fluid (e.g., a saline solution) and then surgical instruments are inserted into the interior of the joint so as to carry out the desired surgical procedure.

In order to visualize what is taking place at the remote interior site, the physician also inserts an endoscope into the patient's body during the endoscopic surgery, together with an appropriate source of illumination. Such an endoscope generally comprises an elongated shaft having a distal end and a proximal end, and at least one internal passageway extending between the distal end and the proximal end. Image capturing means are disposed at the distal end of the shaft and extend through the shaft's at least one internal passageway, whereby the image capturing means can capture an image of a selected region located substantially adjacent to the distal end of the shaft and convey that image to the proximal end of the shaft. Viewing means are in turn disposed adjacent to the proximal end of the shaft, whereby the image obtained by the image capturing means can be conveyed to a display device which is viewed by the physician.

Endoscopes of the sort described above are generally sufficient to permit the physician to carry out the desired endoscopic procedure. However, certain problems have been encountered when using such endoscopes in surgical procedures.

For example, endoscopes of the sort described above generally have a fairly limited field of view. As a result, the physician typically cannot view the entire surgical field in a single image. This can mean that the physician may not see an important development as soon as it occurs, and/or that the physician must expend precious time and energy constantly redirecting the endoscope to different anatomical regions.

Visualization problems can also occur due to the difficulty of providing proper illumination within a remote interior site.

Also, visualization problems can occur due to the presence of intervening structures (e.g., fixed anatomical structures, moving debris, flowing blood, the presence of vaporized tissue when cauterizing in laparoscopic surgery, the presence of air bubbles in a liquid medium in the case of arthroscopic surgery, etc.).

It has also been found that it can be very difficult for the physician to navigate the endoscope about the anatomical structures of interest, due to the relative ambiguity of various anatomical structures when seen through the endoscope's aforementioned limited field of view and due to the aforementioned visualization problems.

OBJECTS OF THE INVENTION

Accordingly, one object of the present invention is to provide an improved anatomical visualization system.

Another object of the present invention is to provide an improved anatomical visualization system which is adapted to enhance a physician's ability to comprehend the nature and location of internal bodily structures during endoscopic visualization.

Still another object of the present invention is to provide an improved anatomical visualization system which is adapted to enhance a physician's ability to navigate an endoscope within the body.

Yet another object of the present invention is to provide an improved anatomical visualization system which is adapted to augment a standard video endoscopic system with a coordinated computer model visualization system so as to enhance the physician's understanding of the patient's interior anatomical structures.

And another object of the present invention is to provide an improved method for visualizing the interior anatomical structures of a patient.

And still another object of the present invention is to provide an improved anatomical visualization system which can be used with remote visualization devices other than endoscopes, e.g., miniature ultrasound probes.

And yet another object of the present invention is to provide an improved visualization system which can be used to visualize remote objects other than interior anatomical structures, e.g., the interiors of complex machines.

And another object of the present invention is to provide an improved method for visualizing objects.

SUMMARY OF THE INVENTION

These and other objects of the present invention are addressed by the provision and use of an improved anatomical visualization system comprising, in one preferred embodiment, a database of pre-existing software objects, wherein at least one of the software objects corresponds to a physical structure which is to be viewed by the system; a real-time sensor for acquiring data about the physical structure when the physical structure is located within that sensor's data acquisition field, wherein the real-time sensor is capable of being moved about relative to the physical structure; generating means for generating a real-time software object corresponding to the physical structure, using data acquired by the sensor; registration means for positioning the real-time software object in registration with the pre-existing software objects contained in the database; and processing means for generating an image from the software objects contained in the database, based upon a specified point of view.

In another preferred form of the invention, the generating means create a software object that corresponds to a disk. The generating means may also be adapted to texture map the data acquired by the sensor onto the disk. Also, the registration means may comprise tracking means that are adapted so as to determine the spatial positioning and orientation of the real-time sensor and/or the physical structure.

In another preferred aspect of the invention, the real-time sensor may comprise an endoscope and the physical structure may comprise an interior anatomical structure. The system may also include either user input means for permitting the user to provide the processing means with the specified point of view, or user tracking means that are adapted to provide the processing means with the specified point of view.

According to another aspect of the invention, the real-time computer-based viewing system may comprise a database of software objects and image generating means for generating an image from the software objects contained in the database, based upon a specified point of view. In accordance with this aspect of the invention, means are also provided for specifying this point of view. At least one of the software objects contained in the database comprises pre-existing data corresponding to a physical structure which is to be viewed by the system, and at least one of the software objects comprises data generated by a real-time, movable sensor. The system further comprises registration means for positioning the at least one software object, comprising data generated by the real-time movable sensor, in registration with the at least one software object comprising pre-existing data corresponding to the physical structure which is to be viewed by the system.

A preferred method for utilizing the present invention comprises: (1) positioning the sensor so that the physical structure is located within that sensor's data acquisition field, and generating a real-time software object corresponding to the physical structure using data acquired by the sensor, and positioning the real-time software object in registration with the pre-existing software objects contained in the database; (2) providing a specified point of view to the processing means; and (3) generating an image from the software objects contained in the database according to that specified point of view.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein.

DETAILED DESCRIPTION OF THE PREFERRED EMBODIMENT

Figure 1:
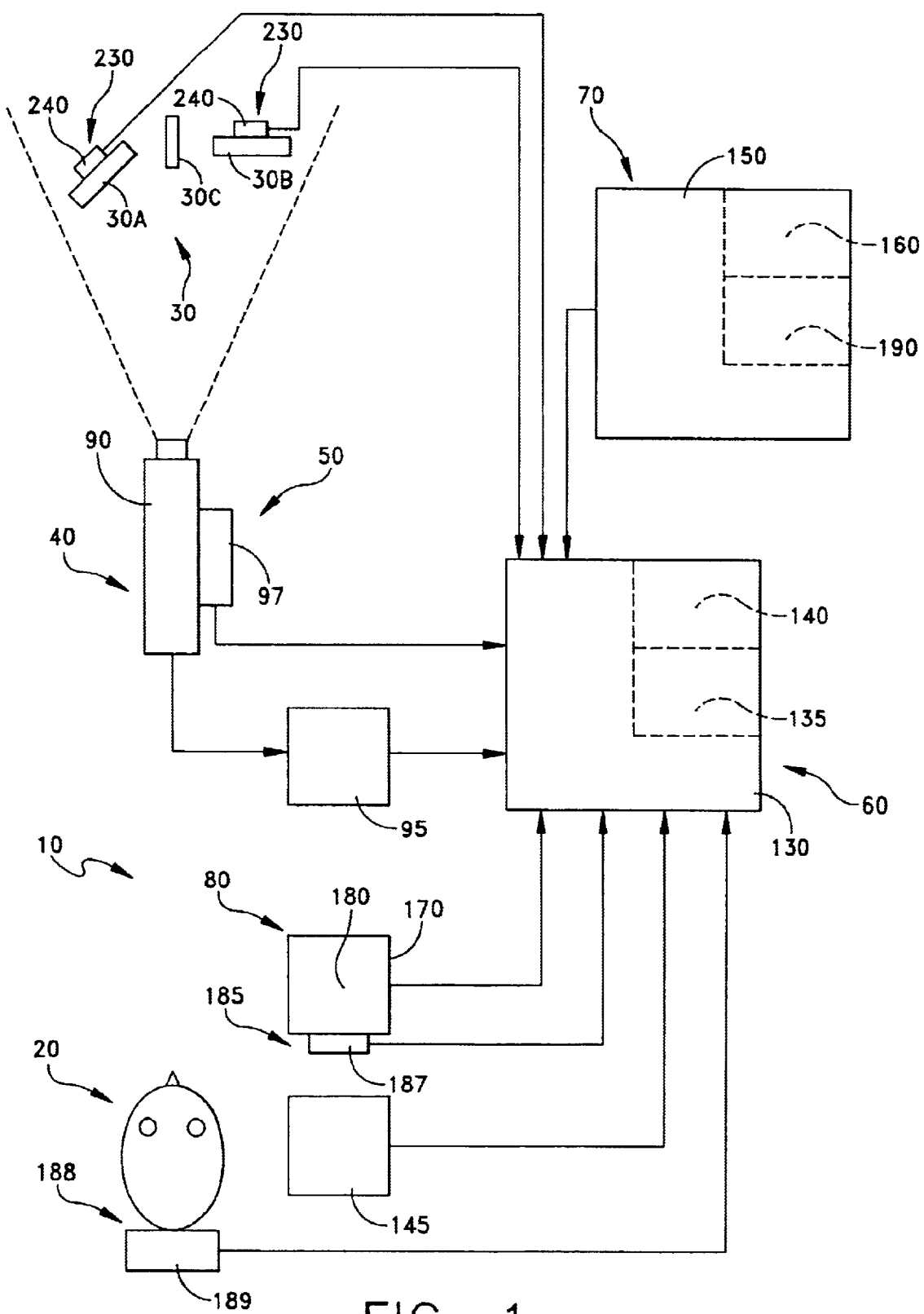
FIG. 1 is a schematic view showing an anatomical visualization system formed in accordance with the present invention.

Looking first at FIG. 1, there is shown an anatomical visualization system 10 which comprises a preferred embodiment of the present invention. Anatomical visualization system 10 is intended to be used by a physician 20 to visually inspect anatomical objects 30 located at an interior anatomical site. By way of example, anatomical visualization system 10 might be used by physician 20 to visually inspect a tibia 30A, a femur 30B and a meniscus 30C located within the knee joint of a patient.

An important aspect of the present invention is the provision of an improved anatomical visualization system which is adapted to augment a standard video endoscopic system with a coordinated computer model visualization system so as to enhance the physician's understanding of the patient's interior anatomical structure.

To that end, anatomical visualization system 10 generally comprises endoscope means 40, endoscope tracking means 50, computer means 60, database means 70 containing 3-D computer models of various objects which are to be visualized by the system, and display means 80.

Endoscope means 40 comprise an endoscope of the sort well known in the art. More particularly, endoscope means 40 comprise an endoscope 90 which comprises (i) a lens arrangement which is disposed at the distal end of the endoscope for capturing an image of a selected region located substantially adjacent to the distal end of the endoscope, and (ii) an appropriate image sensor, e.g., a charge coupled device ("CCD") element or video tube, which is positioned on the endoscope so as to receive an image captured by the lens arrangement and to generate corresponding video signals which are representative of the captured image.

The video signals output from endoscope 90 are fed as an input into computer means 60. However, inasmuch as endoscope 90 will generally output its video signals in analog form and inasmuch as computer means 60 will generally require its video signal input to be in digital form, some conversion of the endoscope's video feed is generally required. In the preferred embodiment, video processing means 95 are provided to convert the analog video signals output by endoscope 90 into the digital video signals required by computer means 60. Video processing means 95 are of the sort well known in the art and hence need not be described in further detail here.

Endoscope tracking means 50 comprise a tracking system of the sort well known in the art. More particularly, endoscope tracking means 50 may comprise a tracking system 97 of the sort adapted to monitor the position and orientation of an object in space and to generate output signals which are representative of the position and orientation of that object. By way of example, tracking system 97 might comprise an optical tracking system, an electromagnetic tracking system, an ultrasonic tracking system, or an articulated linkage tracking system, among other alternatives. Such tracking systems are all well known in the art and hence need not be described in further detail here. Tracking system 97 is attached to endoscope 90 such that the output signals generated by tracking system 97 will be representative of the spatial positioning and orientation of endoscope 90. The output signals generated by tracking system 97 is fed as an input into computer means 60.

Computer means 60 comprise a digital computer 130 of the sort adapted for high speed processing of computer graphics. Such digital computers are well known in the art. By way of example, digital computer 130 might comprise a Silicon Graphics Reality Engine digital computer, or it might comprise a Silicon Graphics Iris Indigo$^2$ Impact digital computer, or it might comprise some equivalent digital computer.

Computer means 60 also comprise the operating system software (schematically represented at 135 in FIG. 1) and the application program software (schematically represented at 140 in FIG. 1) required to cause computer 130 to operate in the manner hereinafter described. In particular, application program software 140 includes image rendering software of the sort adapted to generate images from the 3-D computer models contained in database means 70 according to a specified point of view. By way of example, where digital computer 130 comprises a Silicon Graphics digital computer of the sort disclosed above, operating system software 135 might comprise the IRIX operating system, and the image rendering software contained in application program software 140 might comprise the IRIS gl image rendering software or the OpenGL image rendering software. Such software is well know in the art. As is also well known in the art, such image rendering software utilizes standard techniques, such as the well-known Z buffer algorithm, to draw images of 3-D computer models according to some specified point of view.

As is well known in the art, computer 130 also typically includes input devices 145 through which physician 20 can interact with the computer. Input devices 145 preferably comprise the sort of computer input devices generally associated with a Silicon Graphics digital computer, e.g., input devices 145 preferably comprise a keyboard, a mouse, etc. Among other things, input devices 145 permit physician 20 to initiate operation of anatomical visualization system 10, to select various system functions, and to supply the system with various directives, e.g., input devices 145 might be used by physician 20 to specify a particular viewing position for which the application program's image rendering software should render a visualization of the 3-D software models contained in database means 70.

Database means 70 comprise a data storage device or medium 150 containing one or more 3-D computer models (schematically illustrated as 160 in FIG. 1) of the anatomical objects 30 which are to be visualized by anatomical visualization system 10. The specific data structure used to store the 3-D computer models 160 will depend on the specific nature of computer 130 and on the particular operating system software 135 and the particular application program software 140 being run on computer 130. In general, however, the 3-D computer models 160 contained in data storage device or medium 150 are preferably structured as a collection of software objects. By way of example, a scanned anatomical structure such as a human knee might be modeled as three distinct software objects, with the tibia being one software object (schematically represented at 30A' in FIG. 4), the femur being a second software object (schematically represented at 30B' in FIG. 4), and the meniscus being a third software object (schematically represented at 30C' in FIG. 4). Such software objects are of the sort well known in the art and may have been created, for example, through post-processing of CT or MRI scans of the patient using techniques well known in the art.

Figure 2:
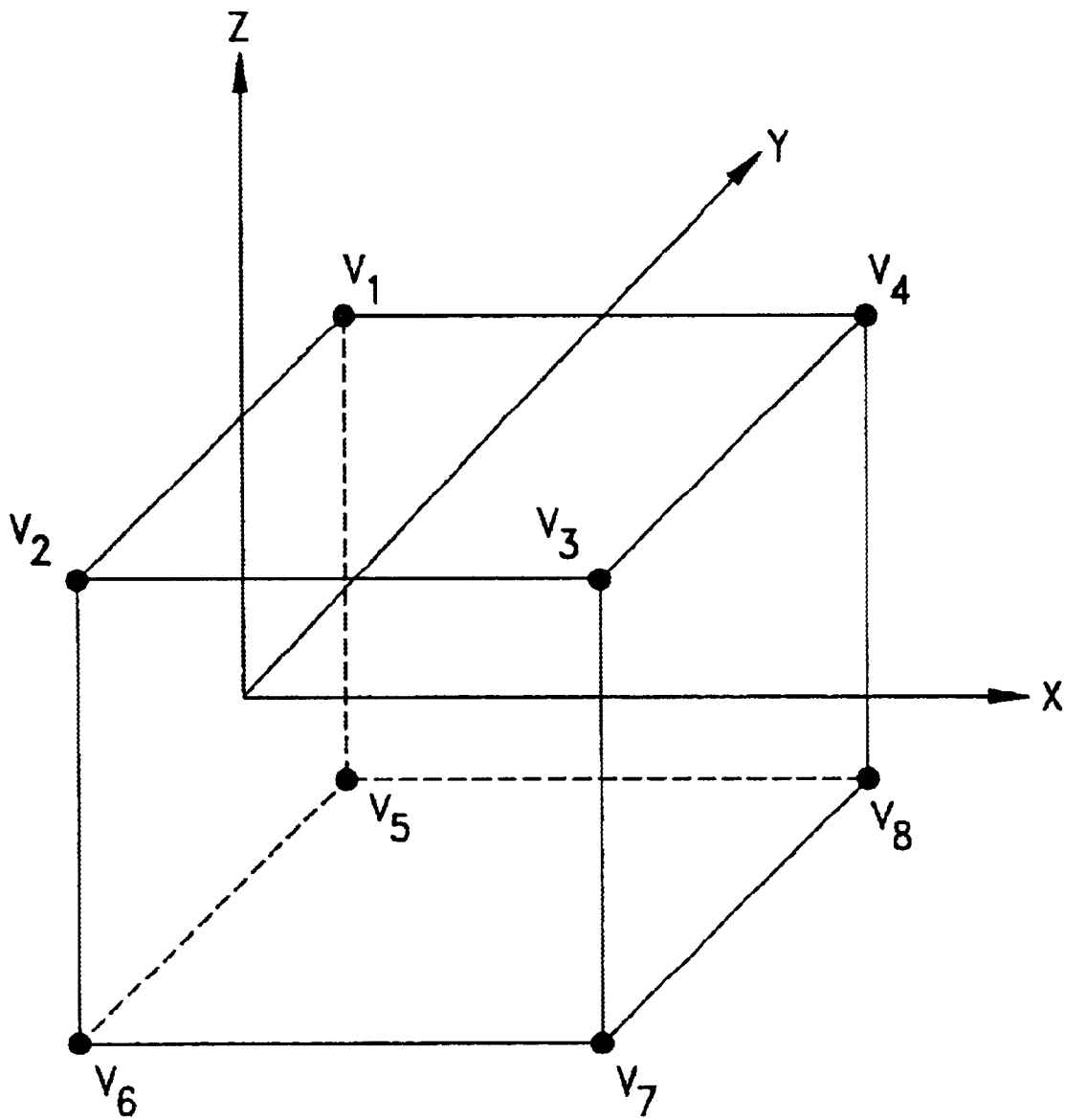
FIG. 2 is a schematic view of a unit cube for use in defining pologonal surface models.
Figure 3:
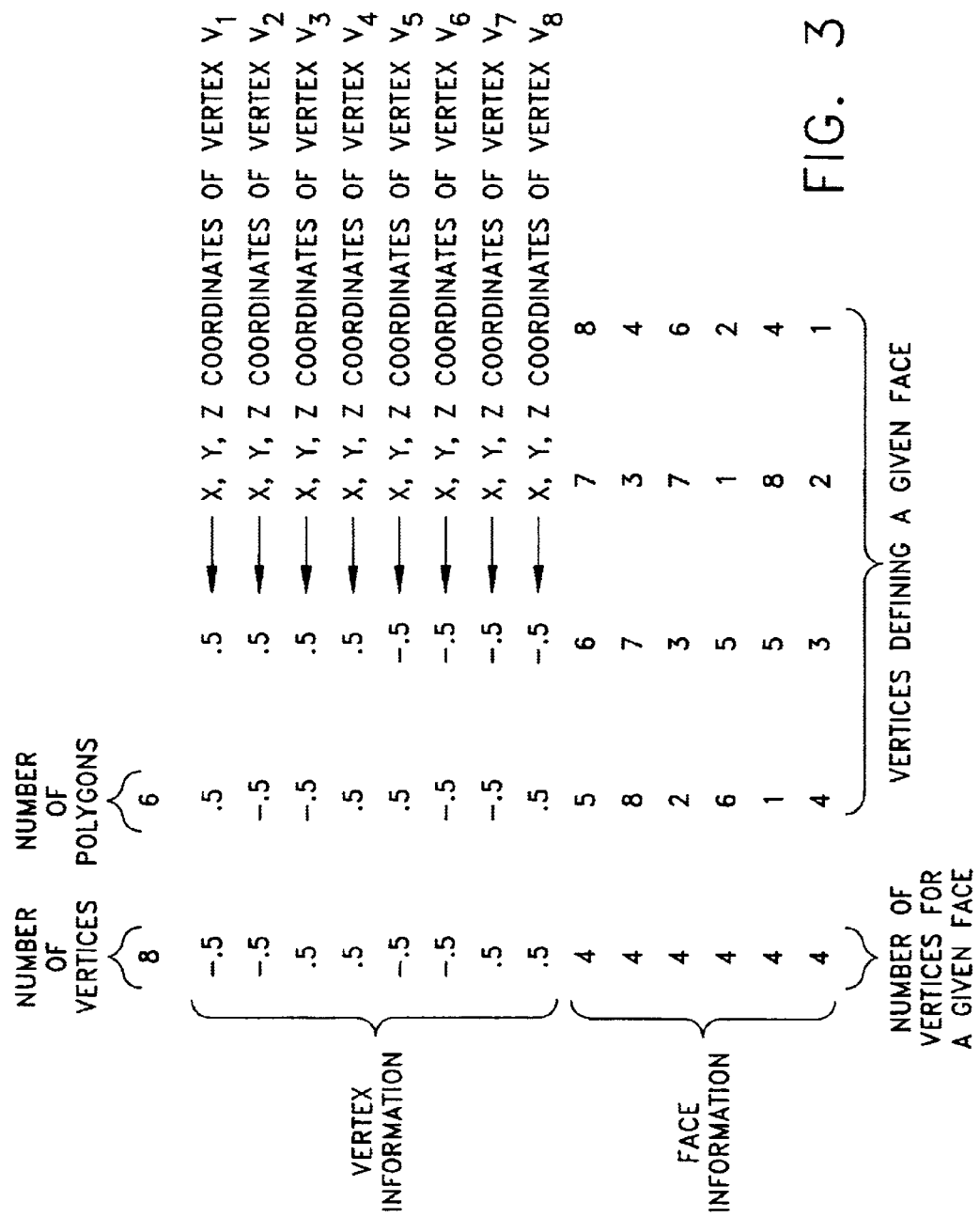
FIG. 3 illustrates the data file format of the pologonal surface model for the simple unit cube shown in FIG. 2.

By way of example, in the case where digital computer 130 comprises a Silicon Graphics digital computer of the sort described above, and where the operating systems's software comprises the IRIX operating system and the application program's image rendering software comprises the Iris gl or OpenGL image rendering software, the 3-D computer models 160 might comprise software objects defined as polygonal surface models, since such a format is consistent with the aforementioned software. By way of further example, FIGS. 2 and 3 illustrate a typical manner of defining a software object using a polygonal surface model of the sort utilized by such image rendering software. In particular, FIG. 2 illustrates the vertices of a unit cube set in an X-Y-Z coordinate system, and FIG. 3 illustrates the data file format of the polygonal surface model for this simple unit cube. As is well known in the art, more complex shapes such as human anatomical structures can be expressed in corresponding terms. It is also to be appreciated that certain digital computers, such as a Silicon Graphics digital computer of the sort described above, can be adapted such that digital video data of the sort output by video processing means 95 can be made to appear on the surface of a polygonal surface model software object in the final rendered image using the well known technique of texture mapping.

Display means 80 comprise a video display of the sort well known in the art. More particularly, display means 80 comprise a video display 170 of the sort adapted to receive video signals representative of an image and to display that image on a screen 180 for viewing by physician 20. By way of example, video display 170 might comprise a television type of monitor, or it might comprise a head-mounted display or a boom-mounted display, or it might comprise any other display device of the sort suitable for displaying an image corresponding to the video signals received from computer means 60, as will hereinafter be described in further detail. In addition, where video display 170 comprises a head-mounted display or a boom-mounted display or some other sort of display coupled to the physician's head movements, physician tracking means 185 (comprising a tracking system 187 similar to the tracking system 97 described above) may be attached to video display 170 and then used to advise computer 130 of the physician's head movements. This can be quite useful, since the anatomical visualization system 10 can use such physician head movements to specify a particular viewing position for which the application program's image rendering software should render a visualization of the 3-D software models contained in database means 70.

In addition to the foregoing, it should also be appreciated that surgeon tracking means 188 (comprising a tracking system 189 similar to the tracking system 97 described above) may be attached directly to surgeon 20 and then used to advise computer 130 of the physician's movements. Again, the anatomical visualization system can use such physician movements to specify a particular viewing position for which the application program's image rendering software should render a visualization of the 3-D software models contained in database means 70.

As noted above, an important aspect of the present invention is the provision of an improved anatomical visualization system which is adapted to augment a standard video endoscopic system with a coordinated computer model visualization system so as to enhance the physician's understanding of the patient's interior anatomical structure. In particular, the improved anatomical visualization system is adapted to augment the direct, but somewhat limited, video images generated by a standard video endoscopic system with the indirect, but somewhat more flexible, images generated by a computer model visualization system.

To this end, and referring now to FIG. 1, database means 70 also comprise one or more 3-D computer models (schematically illustrated at 190 in FIG. 1) of the particular endoscope 90 which is included in anatomical visualization system 10. Again, the specific data structure used to store the 3-D computer models 190 representing endoscope 90 will depend on the specific nature of computer 130 and on the particular operating system software 135 and the particular application program software 140 being run on computer 130. In general, however, the 3-D computer models 190 contained in data storage device or medium 150 are preferably structured as a pair of separate but interrelated software objects, where one of the software objects represents the physical embodiment of endoscope 90, and the other of the software objects represents the video image acquired by endoscope 90.

More particularly, the 3-D computer models 190 representing endoscope 90 comprises a first software object (schematically represented at 90A' in FIG. 4) representative of the shaft of endoscope 90.

Figure 11:
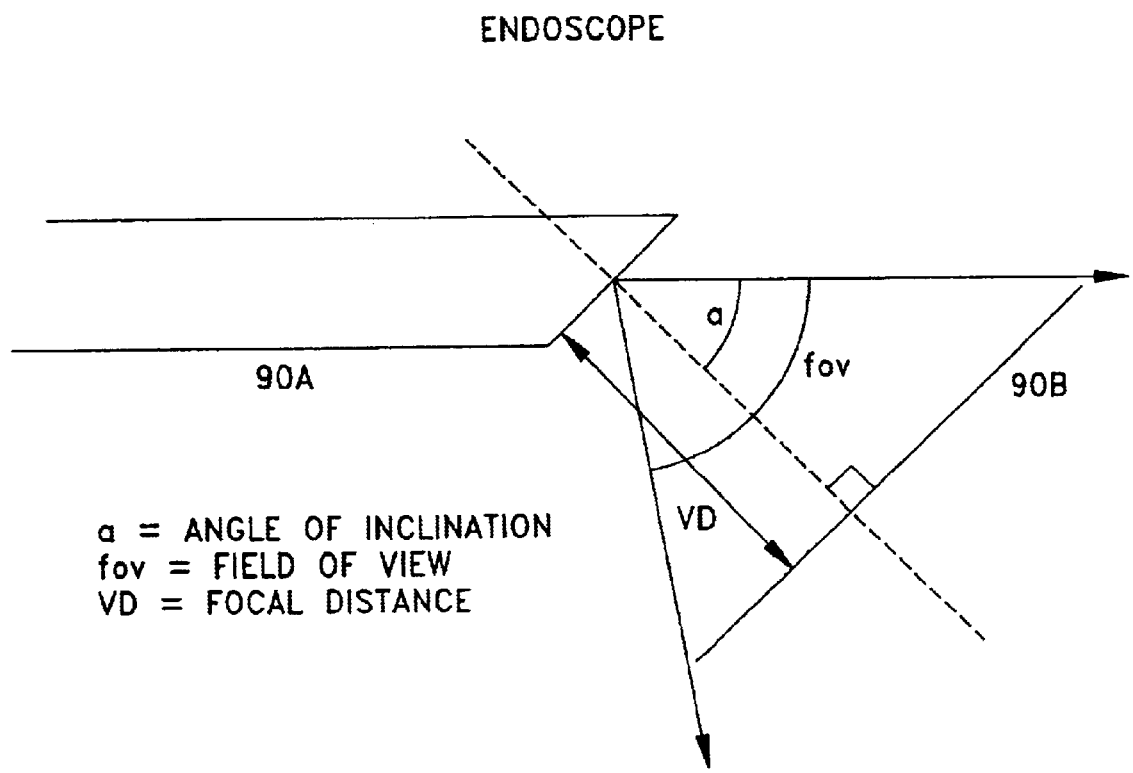
FIG. 11 shows how the optical parameters for an encdoscope can define the relationship between the endoscope 90A' and the disk 90B'.

The 3-D computer models 190 representing endoscope 90 also comprises a second software object (schematically represented at 90B' in FIG. 4) which is representative of the video image acquired by endoscope 90. More particularly, second software object 90B' is representative of a planar disk defined by the intersection of the endoscope's field of view with a plane set perpendicular to the center axis of that field of view, wherein the plane is separated from the endoscope by a distance equal to the endoscope's focal distance. See, for example, FIG. 11, which shows how the optical parameters for an endoscope can define the relationship between the endoscope 90A' and the disk 90B'. In addition, and as will hereinafter be described in further detail, the anatomical visualization system 10 is arranged so that the video signals output by endoscope 90 are, after being properly transformed by video processing means 95 into the digital data format required by digital computer 130, texture mapped onto the planar surface of disk 90B'. Thus it will be appreciated that software object 90B' will be representative of the video image acquired by endoscope 90.

Furthermore, it will be appreciated that the two software objects 90A' and 90B' will together represent both the physical structure of endoscope 90 and the video image captured by that endoscope.

Figure 10:
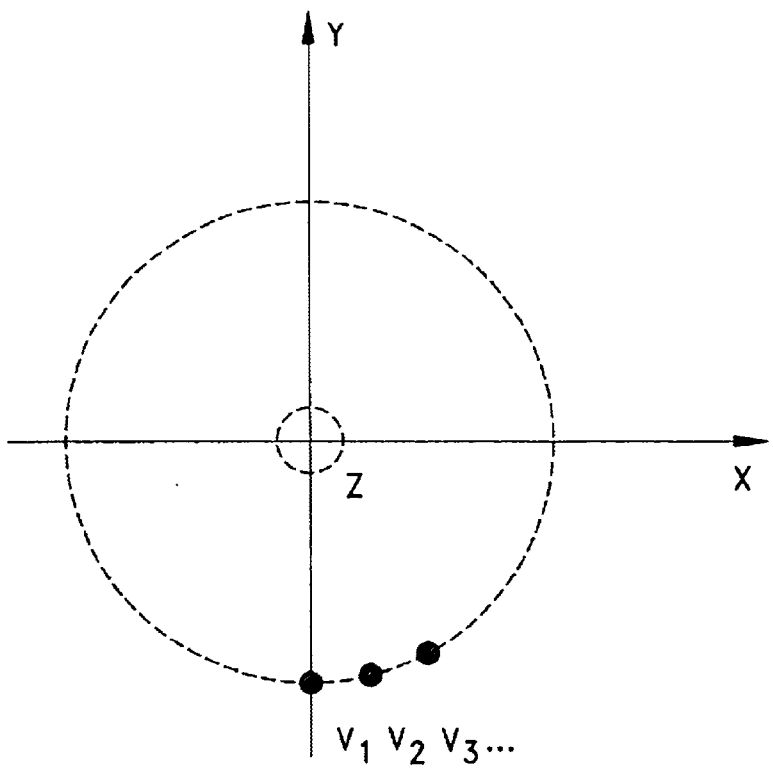
FIG. 10 is a schematic representation of a unit disk software object where the disk is defined in the X-Y plane and has a diameter of 1.

By way of example, in the case where digital computer 130 comprises a Silicon Graphics computer of the sort described above, and where the operating system's software comprises the IRIX operating system and the application program's image rendering software comprises the Iris gl or OpenGL image rendering software, the 3-D computer models 190 might comprise software objects defined as polygonal surface models, since such a format is consistent with the aforementioned software. Furthermore, in a manner consistent with the aforementioned software, UV texture mapping parameters are established for each of the vertices of the planar surface disk 90B' and the digitized video signals from endoscope 90 are assigned to be texture map images for 90B'. See, for example, FIG. 10, which is a schematic representation of a unit disk software object where the disk is defined in the X-Y plane and has a diameter of 1.

It is important to recognize that, so long as the optical characteristics of endoscope 90 remain constant, the size and positional relationships between shaft software object 90A' and disk software object 90B' will also remain constant. As a result, it can sometimes be convenient to think of shaft software object 90A' and disk software object 90B' as behaving like a single unit, e.g., when positioning the software objects 90A' and 90B' within 3-D computer models.

In accordance with the present invention, once the anatomical 3-D computer models 160 have been established from anatomical software objects 30A', 30B' and 30C' (representative of the anatomical objects 30A, 30B, and 30C which are to be visualized by the system), and once the endoscope 3-D computer models 190 have been established from the endoscope software objects 90A' and 90B' (representative of the endoscope and the video image captured by that endoscope), the various software objects are placed into proper registration with one another using techniques well known in the art so as to form a cohesive database for the application program's image rendering software.

Stated another way, a principal task of the application program is to first resolve the relative coordinate system of all the various software objects of anatomical 3-D computer models 160 and of endoscope 3-D computer models 190, and then to use the application program's image rendering software to merge these elements into a single composite image combining both live video images derived from endoscope 90 with computer generated images derived from the computer graphics system.

In this respect it will be appreciated that anatomical software objects 30A', 30B' and 30C' will be defined in 3-D computer models 160 in the context of a particular coordinate system (e.g., the-coordinate system established when the anatomical software objects were created), and endoscope software objects 90A' and 90B will be defined in the context of the coordinate system established by endoscope tracking means 50.

Various techniques are well known in the art for establishing the proper correspondence between two such coordinate systems. By way of example, where anatomical objects 30A', 30B' and 30C' include unique points of reference which are readily identifiable both visually and within the anatomical 3-D computer models 160, the tracked endoscope can be used to physically touch those unique points of reference; such physical touching with the tracked endoscope will establish the location of those unique points of reference within the coordinate system of the endoscope, and this information can then be used to map the relationship between the endoscope's coordinate system and the coordinate system of the 3-D computer models 160. Alternatively, proper software object registration can also be accomplished by pointing endoscope 90 at various anatomical objects 30A, 30B and 30C and then having the system execute a search algorithm to identify the "virtual camera" position that matches the "real camera" position. Still other techniques for establishing the proper correspondence between two such coordinate systems are well known in the art.

Figure 4:
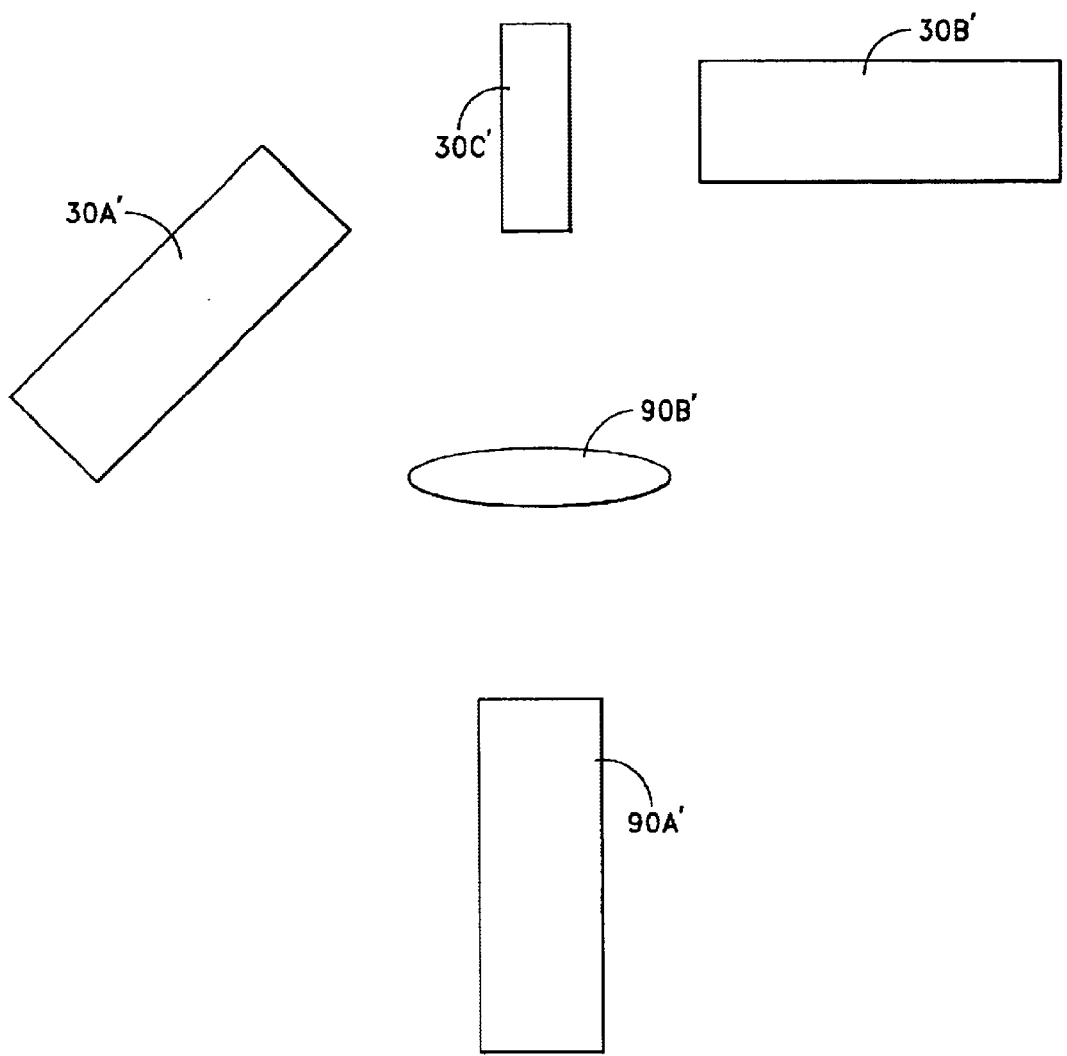
FIG. 4 illustrates a system of software objects.

Once the proper correspondence has been established between all of the coordinate systems, anatomical software objects 30A', 30B' and 30C' and endoscope software objects 90A' and 90B' can be considered to simultaneously coexist in a single coordinate system in the manner schematically illustrated in FIG. 4, whereby the application program's image rendering software can generate images of all of the system's software objects (e.g., 30A', 30B', 30C', 90A' and 90B') according to some specified point of view.

Figure 5:
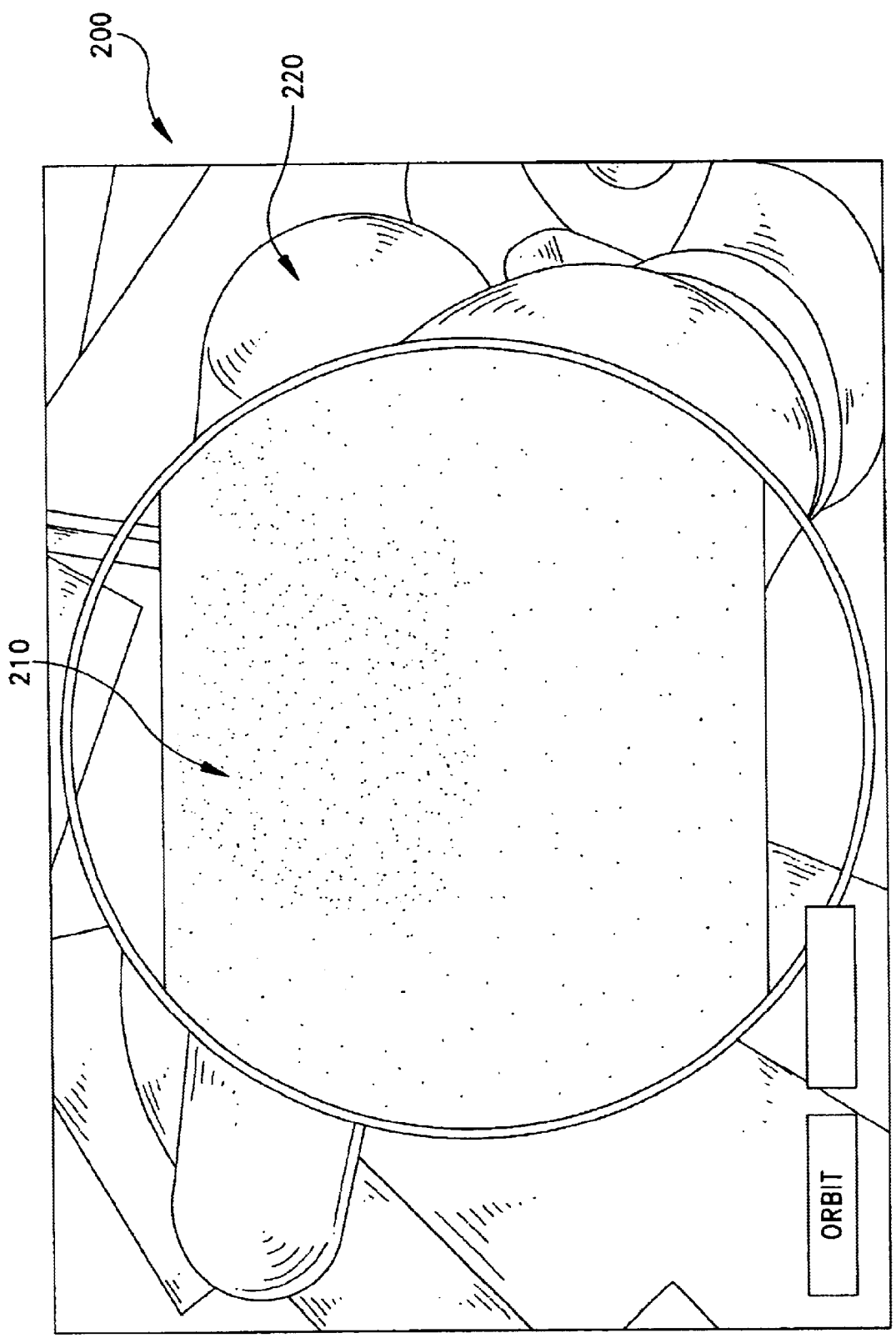
FIG. 5 illustrates an image rendered by the anatomical visualization system.

Furthermore, inasmuch as the live video output from endoscope 90 is texture mapped onto the surface of disk 90B', the images generated by the application program's image rendering software will automatically integrate the relatively narrow field of view, live video image data provided by endoscope 90 with (ii) the wider field of view, computer model image data which can be generated by the system's computer graphics. See, for example, FIG. 5, which shows a composite image 200 which combines video image data 210 obtained from endoscope 90 with computer model image data 220 generated by the system's computer graphics.

It is to be appreciated that, inasmuch as endoscope tracking means 50 are adapted to continuously monitor the current position of endoscope 90 and report the same to digital computer 130, digital computer 130 can continuously update the 3-D computer models 190 representing endoscope 90. As a result, the images generated by the application program's image rendering software will remain accurate even as endoscope 90 is moved about relative to anatomical objects 30.

In addition to the foregoing, it should also be appreciated that anatomical object tracking means 230 (comprising a tracking system 240 generally similar to the tracking system 97 described above) may be attached to one or more of the anatomical objects 30A, 30B and 30C and then used to advise computer 130 of the current position of that anatomical object (see, for example, FIG. 1, where tracking system 240 has been attached to the patient's tibia 30A and femur 30B). As a result, digital computer 130 can continually update the 3-D computer models 160 representing the anatomical objects. Accordingly, the images generated by the application program's image rendering software will remain accurate even as tibia 30A and/or femur 30B move about relative to endoscope 90.

Figure 6:
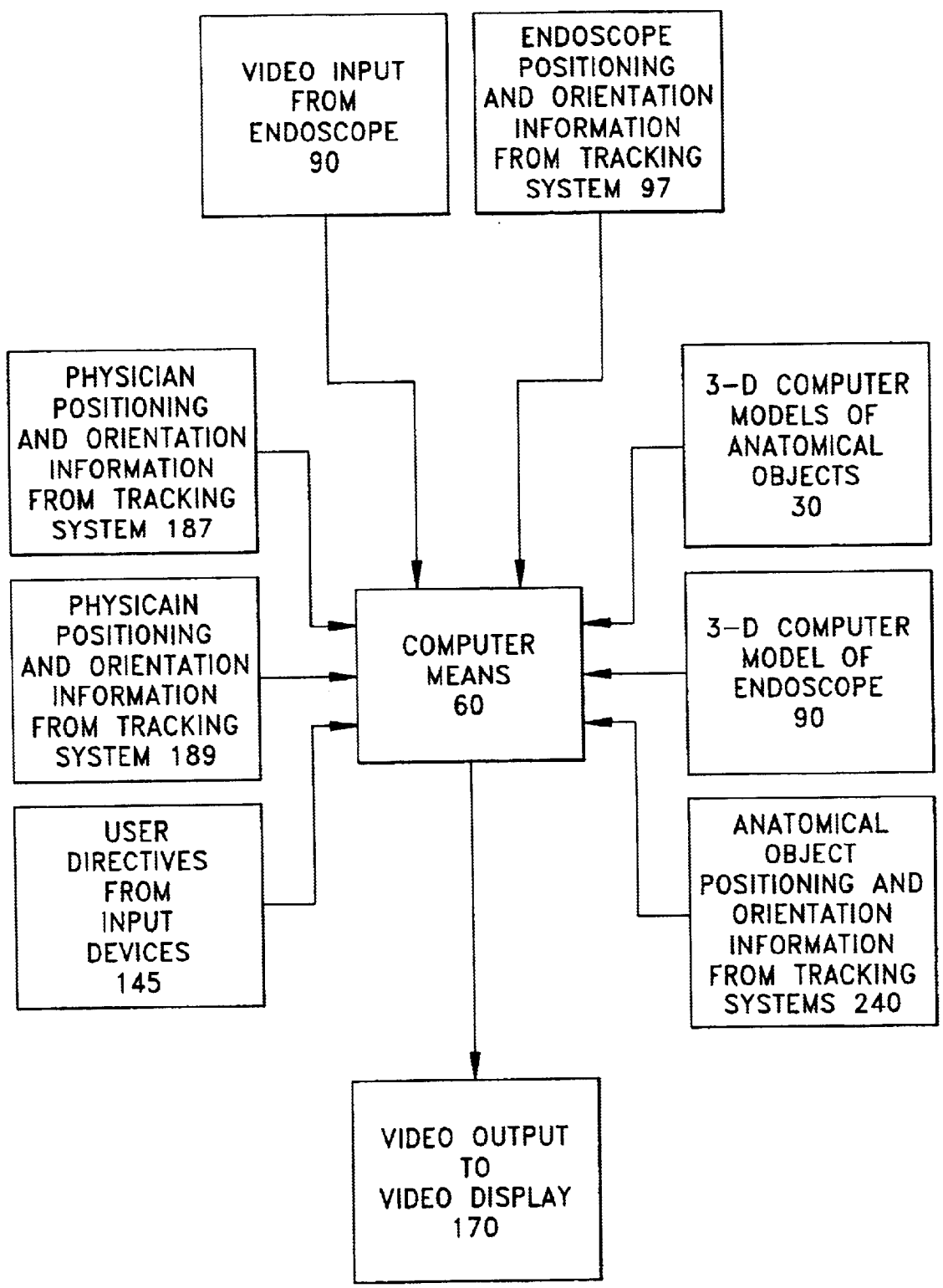
FIG. 6 illustrates how various elements of system data are input into computer means 60 in connection with the system's generation of output video for display on video display 170.

FIG. 6 provides additional details on how various elements of system data are input into computer means 60 in connection with the system's generation of output video for display on video display 170.

Figure 7:
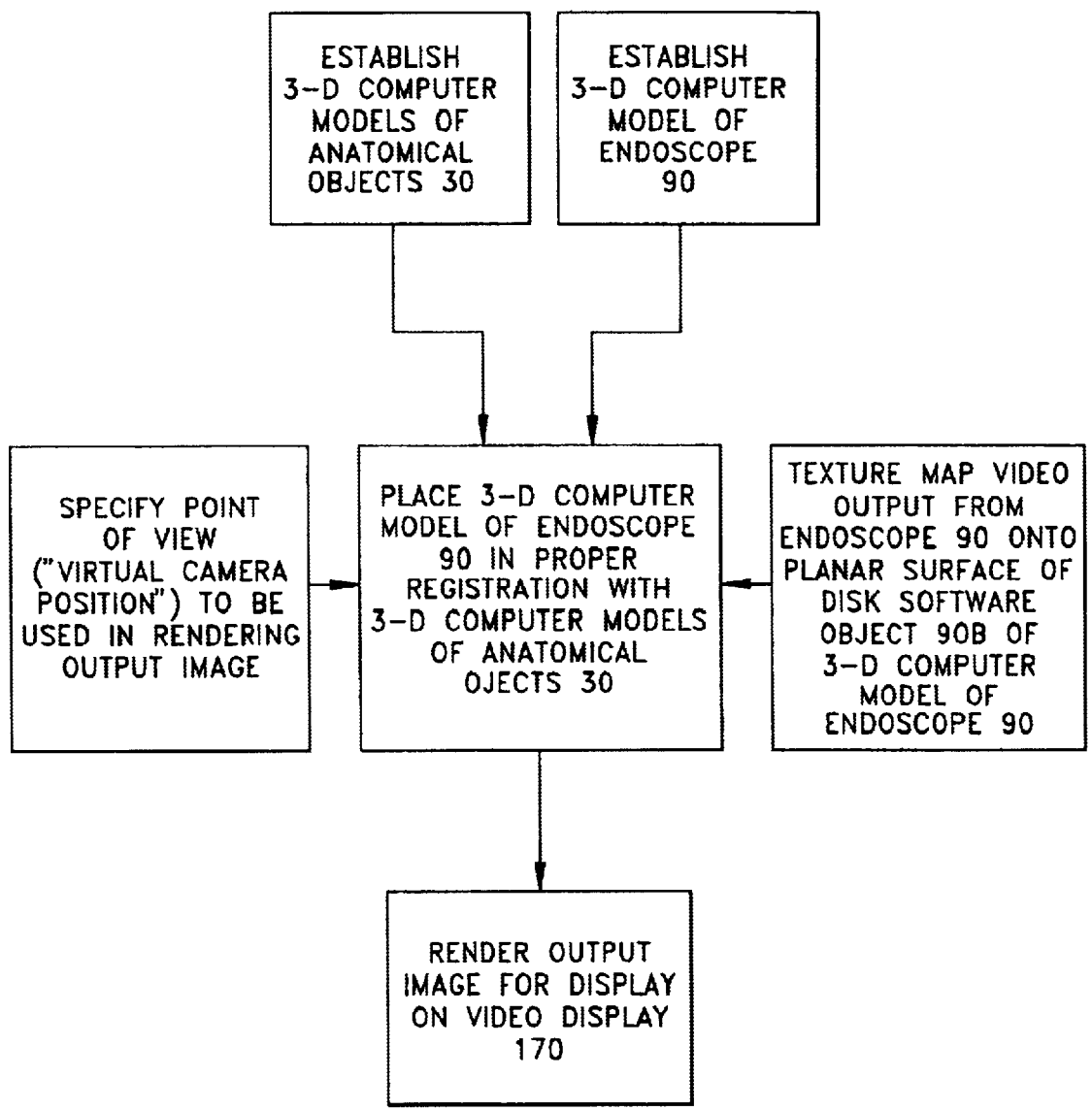
FIG. 7 illustrates additional details on the methodology employed by anatomical visualization system 10 in connection in rendering a video output image for display on video display 170.

FIG. 7 provides additional details on the methodology employed by anatomical visualization system 10 in connection with rendering a video output image for display on video display 170.

Figure 8:
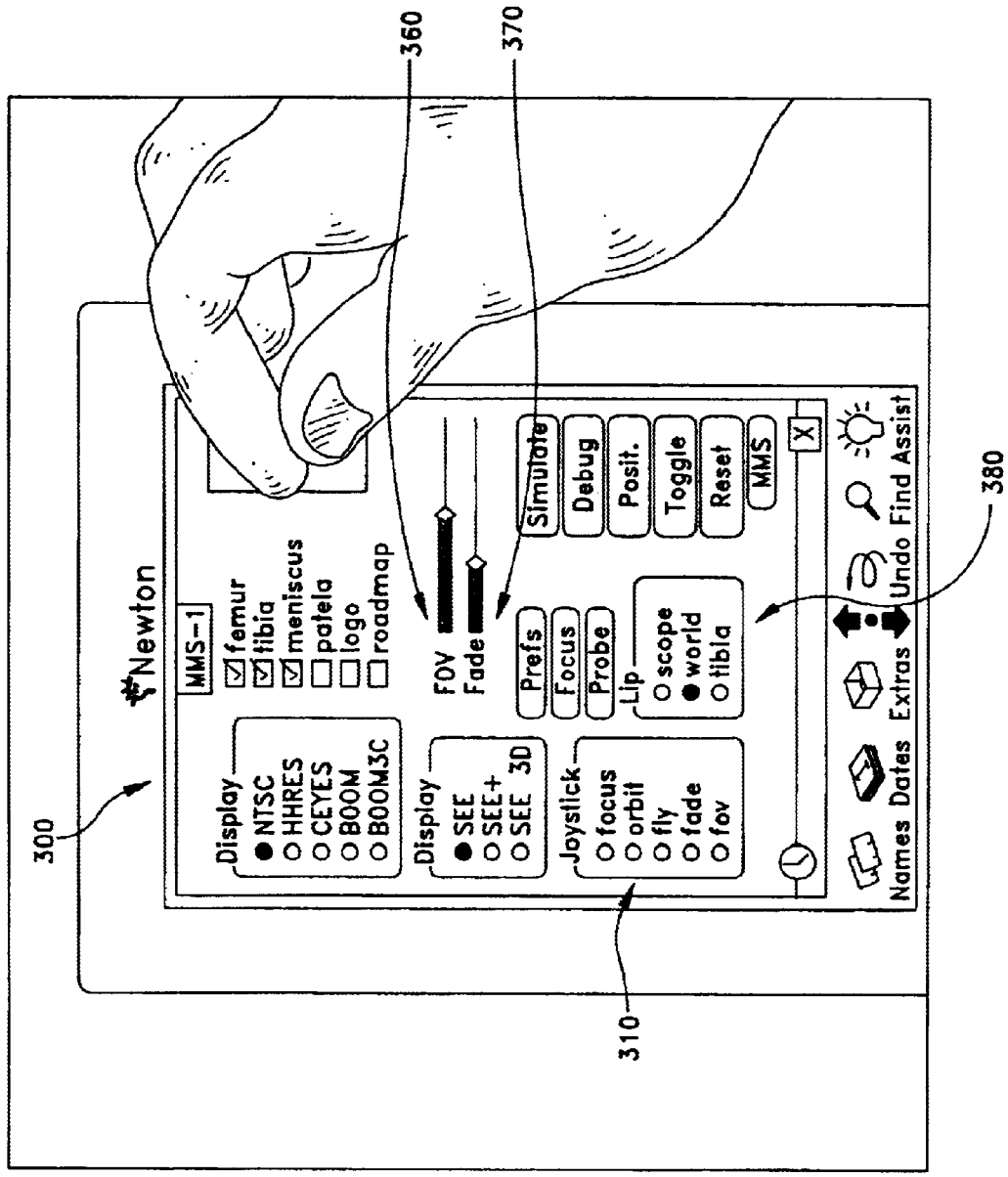
FIG. 8 illustrates a typical screen display provided in accordance with the present invention.
Figure 9:
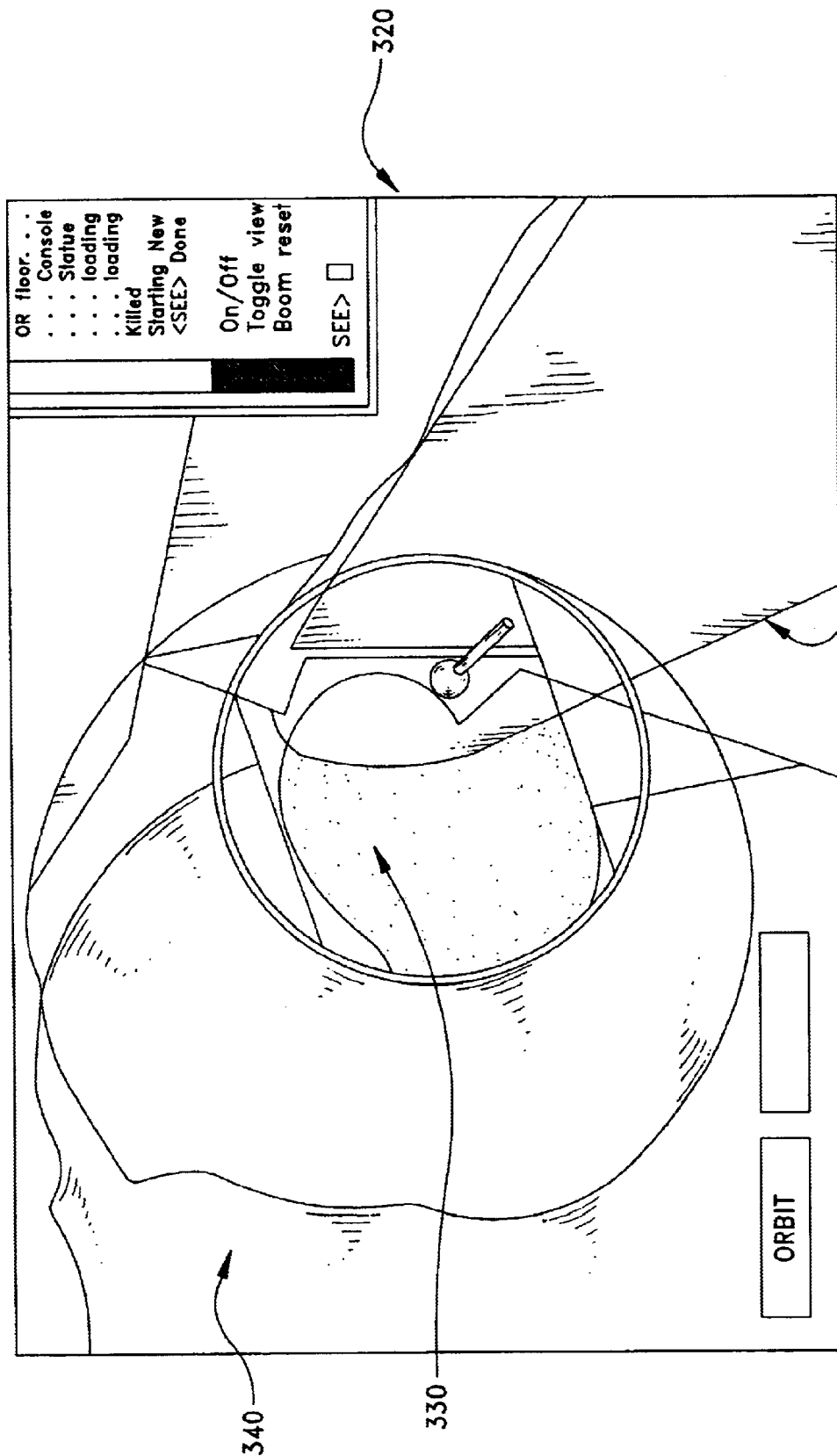
FIG. 9 illustrates an image rendered by the anatomical visualization system.

The application program software 140 of computer means 60 is configured so as to enable physician 20 to quickly and easily specify a particular viewing position (i.e., a "virtual camera" position in computer graphics terminology) for which the application program's image rendering software should render a visualization of the 3-D software models contained in database means 70. By way of illustration, FIG. 8 shows a typical Apple Newton screen display 300 which provides various user input choices for directing the system's "virtual camera". For example, physician 20 may select one of the joystick modes as shown generally at 310 for permitting the user to use a joystick-type input device to specify a "virtual camera" position for the system. Alternatively, physician 20 may choose to use physician tracking means 185 or 187 to specify the virtual camera position for the system, in which case movement of the physician will cause a corresponding change in the virtual camera position. Using such tools, the physician may specify a virtual camera position disposed at the very end of the endoscope's shaft, whereby the endoscope's shaft is not seen in the rendered image (see, for example, FIG. 5), or the user may specify a virtual camera position disposed midway back along the length of the shaft, whereby a portion of the endoscope's shaft will appear in the rendered image. See, for example, FIG. 9, which shows a composite image 320 which combines video image data 330 obtained from endoscope 90 with computer model image data 340 generated by the system's computer graphics, and further wherein a computer graphic representation 350 of the endoscope's shaft appears on the rendered image.

It is to be appreciated that physician 20 may specify a virtual camera position which is related to the spatial position and orientation of endoscope 90, in which case the virtual camera position will move in conjunction with endoscope 90. Alternatively, physician 20 may specify a virtual camera position which is not related to the spatial position and orientation of endoscope 90, in which case the virtual camera position will appear to move independently of endoscope 90.

Still referring now to FIG. 8, it is also possible for physician 20 to use slider control 360 to direct the application program's image rendering software to adjust the field of view set for the computer graphic image data 340 (see FIG. 9) generated by the system's computer graphics.

Additionally, it is also possible for physician 20 to use slider control 370 to direct the application program's image rendering software to fade the density of the video image which is texture mapped onto the face of disk software object 90B'. As a result of such fading, the face of the system's disk can be made to display an overlaid composite made up of both video image data and computer graphic image data, with the relative composition of the image being dictated according to the level of fade selected.

It is also to be appreciated that, inasmuch as the display image rendered by anatomical visualization system 10 is rendered from a collection of software objects contained in 3-D computer models, it is possible to render the display image according to any preferred vertical axis. Thus, for example, and referring now to control 380 in FIG. 8, it is possible to render the display image so that endoscope 90 provides the relative definition of "up", or so that the real world provides the relative definition of "up", or so that some other object (e.g., the principal longitudinal axis of the patient's tibia) provides the relative definition of "up".

It is also to be appreciated that anatomical visualization system 10 can be configured to work with video acquisition devices other than endoscopes. For example, the system can be configured to work with miniature ultrasound probes of the sort adapted for insertion into a body cavity. In this situation the video output of the miniature ultrasound probe would be texture mapped onto the face of disk software object 90B'. Alternatively, other types of video acquisition devices could be used in a corresponding manner.

Also, it is possible to use the foregoing visualization system to render images of objects other than anatomical structures. For example, the system would be used to provide images from the interior of complex machines, so long as appropriate 3-D computer models are provided for the physical structures which are to be visualized.

In the preceding description, anatomical 3-D computer models 160 were created from software objects 30A', 30B', 30C' representing anatomical objects 30A, 30B, 30C; and endoscope 3-D computer models 190 were created from endoscope software objects 90A' and 90B' representing endoscope shaft 90A and endoscope viewing field 90B; and the various software objects were placed into proper registration with one another using techniques well known in the art so as to form a cohesive database for the application program's image rendering software.

In this respect it should be appreciated that it is also possible to create computer models of objects in addition to anatomical objects 30A, 30B, 30C and endoscope 90 and to place those computer models into the system's database for selective viewing by the system's image rendering software.

Figure 12:
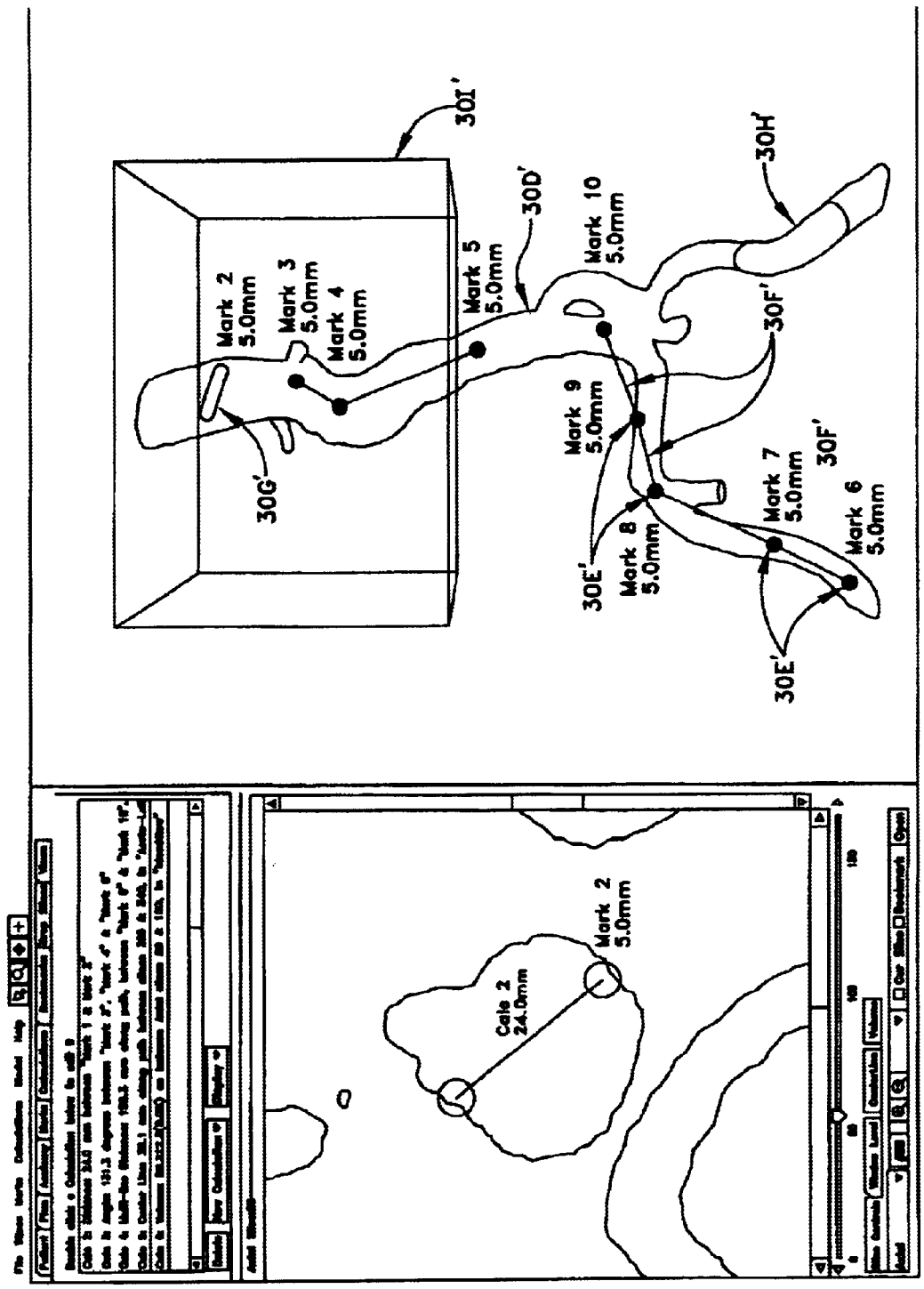
FIG. 12 is a schematic representation of a software object representing the aorta of a patient.

By way of example, and looking now at FIG. 12, there is shown a software object 30D' representing the aorta of a patient. Also shown is a series of markers 30E' placed into the system (e.g., by a human operator using a mouse) and a series of line segments 30F' extending between selected ones of the markers 30E'. These markers 30E' and line segments 30F' may be used to plan a surgical procedure, to determine anatomical lengths or angles, etc.

Also shown is a straight tube 30G' which may also be used for planning and measurement purposes, etc., a curved tube 30H' which may be used for planning and measurement purposes, and a box 30I' which may be used for planning and measurement purposes, e.g., for volume calculations.

Figure 13:
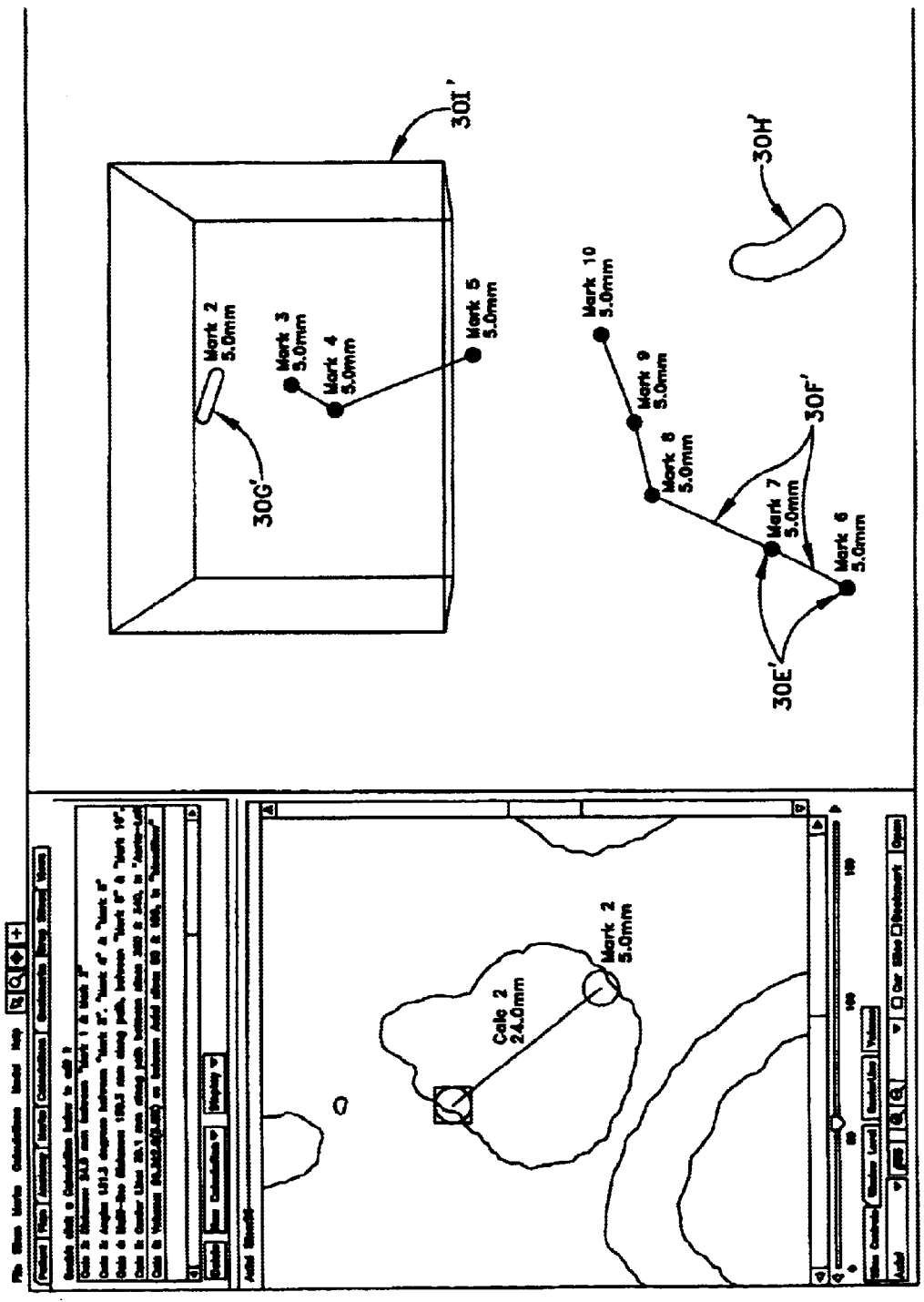
FIG. 13 is a schematic representation of the software object of FIG. 12 in which the aorta has been rendered transparent.

FIG. 13 is similar to FIG. 12, except that aorta 30D' has been rendered transparent.

In addition, other geometric elements such as curved lines, intersecting lines, etc. may also be provided for planning and measurement purposes.

Figure 14:
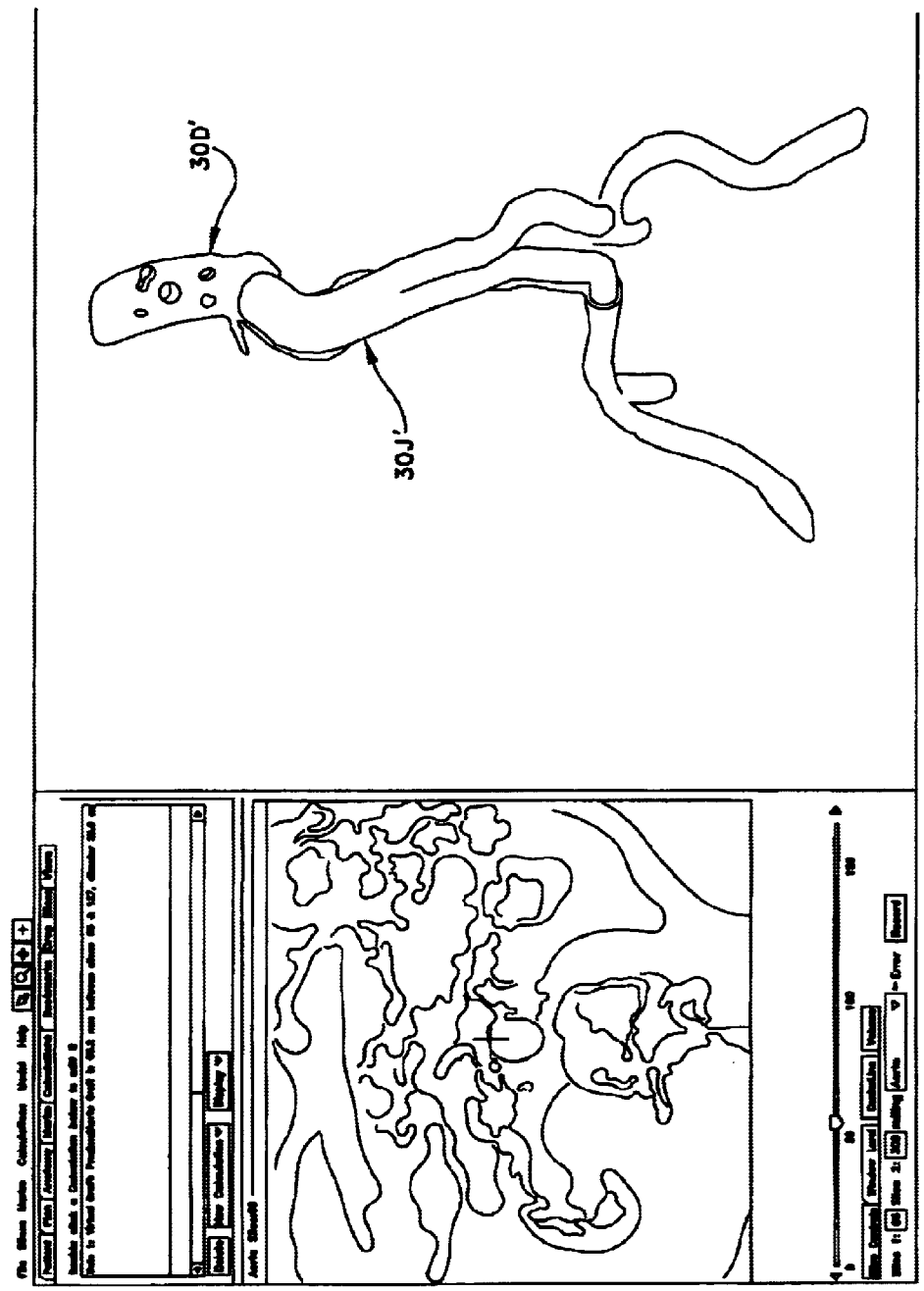
FIG. 14 is a schematic representation of a virtual graft deployed in the aorta of FIG. 12.

Significantly, it is also possible to insert into the system software objects representing virtual grafts, virtual implants, etc. By way of example, in FIG. 14 there is shown a virtual graft 30J' which represents an arterial stent which may be deployed in the aorta, e.g., to treat an aortic aneurysm.

It is also to be understood that the present invention is by no means limited to the particular construction herein set forth, and/or shown in the drawings, but also comprises any modifications or equivalents within the scope of the claims.

What is claimed is:

1. A real-time computer-based viewing system comprising:

a database of pre-existing software objects, wherein at least one of said software objects corresponds to a physical structure which is to be viewed by said system and at least one of said software objects corresponds to a graft which is to be deployed adjacent said physical structure;

a real-time sensor for acquiring data about said physical structure when said physical structure is located within that sensor's data acquisition field, wherein said sensor is capable of being moved about relative to said physical structure;

generating means for generating an additional software object corresponding to said physical structure using data acquired by said sensor;

registration means for positioning said additional software object in registration with said pre-existing software objects contained in said database; and processing means for generating an image from said software objects contained in said database, based upon a specified point of view.

* * * * *